US006969468B2

(12) United States Patent
Stone et al.

(10) Patent No.: US 6,969,468 B2
(45) Date of Patent: Nov. 29, 2005

(54) METHOD AND APPARATUS FOR ISOLATING A COMPONENT FROM A FLUID MIXTURE

(75) Inventors: Richard Stone, Merseyside (GB); Richard Mark Dowdeswell, Cheshire (GB); Mohammed El Hassan Amrani, Manchester (GB)

(73) Assignee: Kaiku Limited, Manchester (GB)

( * ) Notice: Subject to any disclaimer, the term of this patent is extended or adjusted under 35 U.S.C. 154(b) by 201 days.

(21) Appl. No.: 10/204,078

(22) PCT Filed: Feb. 16, 2001

(86) PCT No.: PCT/GB01/00641

§ 371 (c)(1),
(2), (4) Date: Nov. 18, 2002

(87) PCT Pub. No.: WO01/61329

PCT Pub. Date: Aug. 23, 2001

(65) Prior Publication Data

US 2003/0106853 A1 Jun. 12, 2003

Related U.S. Application Data
(60) Provisional application No. 60/183,306, filed on Feb. 17, 2000.

(30) Foreign Application Priority Data

Feb. 16, 2000 (GB) .............................. 0003440

(51) Int. Cl.⁷ ............................ G01R 27/08; C02F 1/00
(52) U.S. Cl. ...................... 210/746; 210/748; 210/767; 324/691
(58) Field of Search ................................ 210/746, 748, 210/767, 198.1, 205, 243; 324/691, 708; 422/82.01, 82.02; 436/150; 73/64.56, 863.21

(56) References Cited

U.S. PATENT DOCUMENTS

| 3,656,055 | A |   | 4/1972  | Jilbert |
|-----------|---|---|---------|---------|
| 4,829,837 | A |   | 5/1989  | Telfer  |
| 4,901,024 | A | * | 2/1990  | Miyake et al. .............. 324/438 |
| 5,357,197 | A | * | 10/1994 | Sorkin ........................ 324/204 |
| 5,415,784 | A | * | 5/1995  | Akutsu et al. .............. 210/746 |
| 6,511,851 | B1| * | 1/2003  | Payne et al. ................ 436/151 |
| 6,690,181 | B1| * | 2/2004  | Dowdeswell et al. ....... 324/691 |

FOREIGN PATENT DOCUMENTS

| DE | 43 11 064   | 10/1994 |
| GB | 1120104     | 7/1968  |
| GB | 2 306 660 A | 5/1997  |
| WO | WO 94/23286 | 10/1994 |
| WO | WO 98 46985 A | 10/1998 |

OTHER PUBLICATIONS

Ayliffe et al., "Electric Impedance Spectroscopy Using Microchannels with Integrated Metal Electrodes," *IEEE Journal of Microelectromechanical Systems*, vol. 8, No. 1, pp. 50–57 (Mar. 1999).

* cited by examiner

*Primary Examiner*—Frank M. Lawrence
(74) *Attorney, Agent, or Firm*—Barbara A. Wrigley; Oppenheimer Wolff & Donnelly LLP

(57) ABSTRACT

The present invention relates to an apparatus and method for measuring a particulate characteristic of a particulate-containing fluid, in particular for monitoring the particulate content of lubricating or hydraulic fluids in a mechanical system in order to diagnose component failure.

31 Claims, 1 Drawing Sheet

METHOD AND APPARATUS FOR ISOLATING A COMPONENT FROM A FLUID MIXTURE

Figure 1:
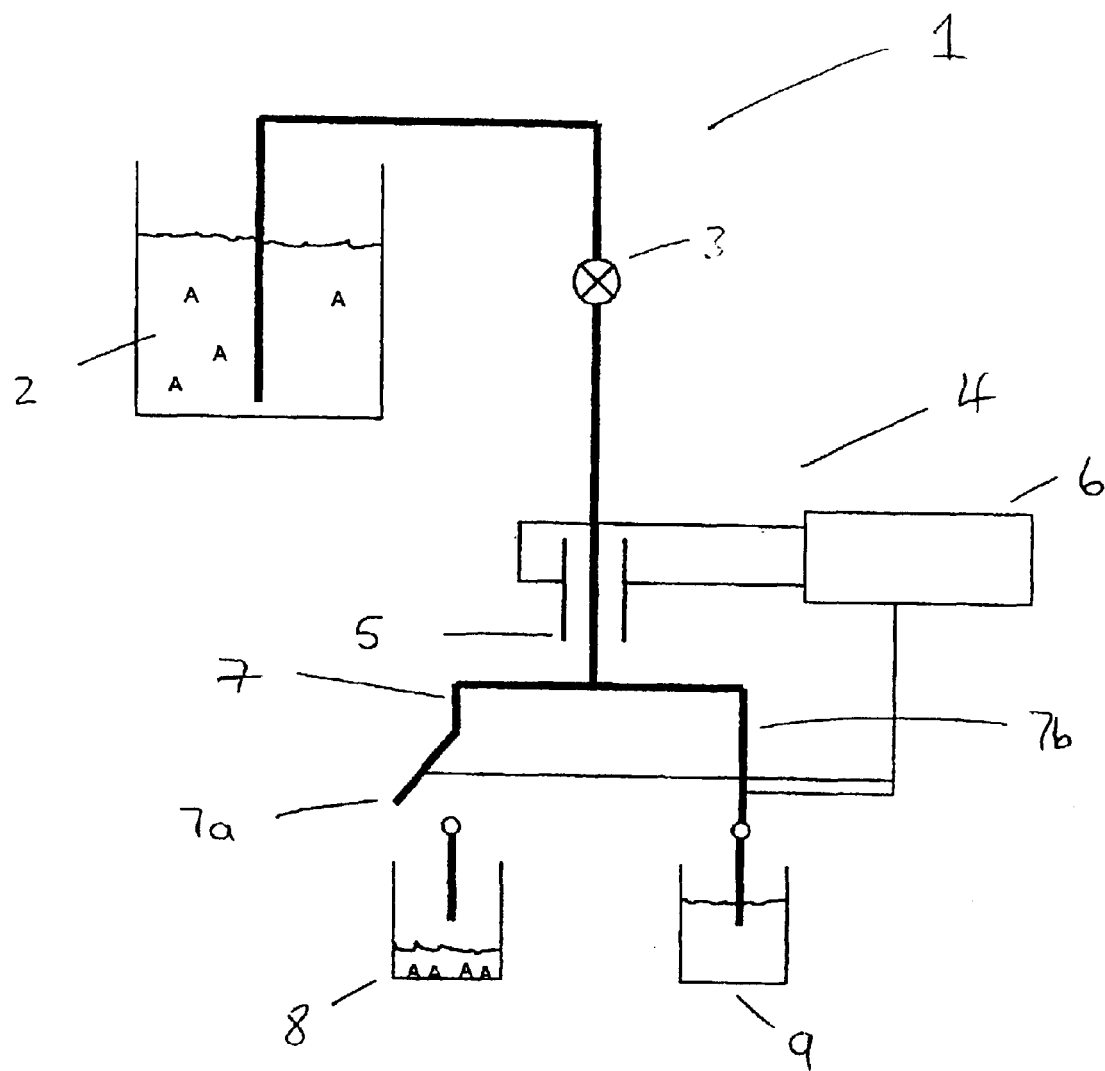

This application claims the benefit to Great Britain Application Serial Number GB 0003440.5 filed on Feb. 16, 2000, to U.S. Application Ser. 60/183,306 filed Feb. 17, 2000, and to PCT Application No. PCT/GB01/00641 (Publication No. WO 01/61329) filed on Feb. 16, 2001.

BACKGROUND OF THE INVENTION

1. Field of the Invention

The present invention relates to a method and apparatus for isolating a component from a fluid mixture, in particular for separating out or concentrating a discrete component of a fluid sample.

Numerous methods may be employed to separate particles from suspensions or to separate different types of particles from each other. Simple physical separation methods such as filtering or centrifugal techniques are commonly used. More sophisticated methods may be employed to separate biological material (eg cells). For example, U.S. Pat. No. 6,013,188 discloses a means for attaching magnetic material to biological cells in a suspension and the use of an applied magnetic field to separate the modified cells from the suspension. Techniques based upon electrophoresis are frequently used as a means for separating cells from one another.

2. Description of the Related Art

WO-A-98/46985 (Payne et al) discloses a method for assessing the composition of a liquid sample using resonance impedance measurements. This enables small changes in bulk electrical properties of the sample to be monitored and correlated with changes in the composition of the liquid.

SUMMARY OF THE INVENTION

The present invention is based on the recognition that the impedance characteristics of a fluid sample which has been made part of a resonant electrical circuit are a useful analytical or manipulative tool. In particular, the impedance characteristics may be used to isolate a component of the sample in a dynamic system.

Thus viewed from one aspect the present invention provides a method for isolating a proportion of a fluid mixture (eg a discrete component such as cells or particles) from the fluid mixture as a whole, said method comprising the steps of:

allowing the fluid mixture to flow through a measuring chamber, applying an electrical signal at one or more frequencies to the proportion of the fluid mixture in the measuring chamber;

measuring an impedance quantity characteristic of the proportion of the fluid mixture in the measuring chamber at the one or more frequencies; and causing the proportion of the fluid mixture to flow to a unique destination remote from the remainder of the fluid mixture when the impedance quantity measured at the one or more frequencies attains a predetermined target (eg is at or near to or exceeds a predetermined target level of the impedance quantity).

The method is particularly advantageous for separating out the components of a very small volume of a fluid sample in a microchamber where the measured impedance quantity (eg spectrum) of that volume of the sample is a fingerprint ie characteristic of the proportion of the fluid in the microchamber.

In a preferred embodiment, the proportion of the fluid mixture is a discrete component such as cells or particles.

In a preferred embodiment, the one or more frequencies at which the impedance quantity is measured includes a resonant frequency. The impedance quantity may be the dissipation factor.

In a preferred embodiment, the electrical signal is applied at each of a plurality of frequencies in a frequency range and the impedance quantity is measured at each of the plurality of frequencies in the frequency range. Preferably the plurality of frequencies includes a resonant frequency. By selecting individual frequencies in a frequency range, the amount of data handling may be reduced and the rate of isolation increased. A suitable number of frequencies may be for example 10. If desired, the plurality of frequencies in the range are sufficient in number to generate an impedance spectrum characteristic of the proportion of the fluid mixture in the measuring chamber. Typically frequencies are selected over a broad frequency range eg 100 Hz to 2 MHz.

In a preferred embodiment, the electrical signal is applied at a single frequency and the impedance quantity is measured at that frequency as the fluid mixture flows through the measuring chamber. The flow rate through the measuring chamber and hence the rate of isolation is generally governed by the time taken to record the process the impedance quantity measurements. Measurements at a single frequency are more rapidly obtained than those at a plurality of frequencies and so that rate of isolation is advantageously optimized. Preferably, the single frequency is at or near to the resonant frequency of the measuring chamber containing the proportion of the fluid mixture. A frequency at or near to the resonant frequency provides the largest variations in the measured impedance quantity and hence a more sensitive method.

Generally speaking, the volume of the measuring chamber is consistent with the dimensions of the discrete component which it is desired to isolate. In a preferred embodiment of the method of the invention, the volume of the proportion of fluid mixture in the measuring chamber is less than 10.sup.−6 liters, preferably less than 10.sup.−9 liters, more preferably less than 10.sup.−12 liters and even as low as about 10.sup.−15 liters. A preferred range for the volume of the proportion of the fluid mixture in the measuring chamber is 10.sup.−6 to 10.sup.−15 liters.

Whilst the applicants do not wish to be bound by theoretical considerations it is noted that by carrying out impedance measurements on very small proportions of fluid mixtures (eg nanoliter or smaller volumes), the fluid mixture was a whole cannot be considered as a homogenous fluid mixture of components but rather a fluid mixture of discrete components. By fabricating a measuring chamber of dimensions similar to those of the discrete components of interest, it is possible to conduct electrical impedance measurements on the discrete components as they pass through the measuring chamber and use of the results to isolate these components. In other words, the measured impedance quantity of the proportion of fluid mixture in the measuring chamber can be considered to be largely characteristic of either a discrete cell or of the discrete fluid medium and the impedance quantity measured for a cell and for the fluid medium will be quite distinct. Such impedance measurements and the instruments for carrying them out have been described generally by Ayliffe et al, IEEE Journal of Micromechanical Systems, 8, 1, 50–57, 1999.

In the method of the invention, the fluid mixture may comprise two or more liquids. Alternatively it may comprise a liquid (or mixture of liquids) with one or more dissolved or suspended components. The fluid mixture may comprise particles or cells suspended in a liquid medium. For example, the fluid mixture may be a blood extract comprising blood cells and liquid medium. Alternatively the fluid mixture may be a solution eg a polymer containing solution. Preferably the fluid mixture is a binary system.

In a preferred embodiment of the method of the invention, the component which it is desired to isolate from a fluid mixture is initially calibrated in the measuring chamber by measuring its impedance quantity (the calibrated impedance quantity) at the one or more frequencies. Preferably the calibrated impedance quantity is measured at a plurality of frequencies to obtain a spectrum (the calibrated impedance spectrum). The calibrated impedance quantity (or spectrum) may be stored in a memory device.

In a preferred embodiment of the method of the invention, the impedance quantity of the proportion of the fluid mixture measured in the measuring chamber is compared with the calibrated impedance quantity. Various steps may be employed for comparing a measured impedance quantity with a calibrated impedance quantity. For example, the measured impedance quantity may be compared with a database of known impedance quantities until an effective match is made. Alternatively, neural network techniques may be used for matching a known impedance quantity with a measured impedance quantity. Alternatively, a subtractive step may be used in which a known impedance quantity is subtracted from the measured impedance quantity. For example, in a binary system of biological cells and liquid media where the known impedance spectrum is that of the liquid media, if the measured impedance spectrum of the proportion of fluid mixture in the measuring chamber is characteristic of liquid media the spectra will cancel and if the measured impedance spectrum of the proportion of fluid mixture in the measuring chambers is characteristic of cells the spectra will not cancel.

In a preferred embodiment of the method of the invention, the step of causing the proportion of the fluid mixture to flow to a unique destination occurs when the impedance quantity measured at the one or more frequencies is substantially the same as the calibrated impedance quantity at the one or more frequencies. Alternatively, the step of causing the proportion of the fluid mixture to flow to a unique destination occurs when the impedance quantity measured at the one or more frequencies is above a predetermined threshold value.

In a preferred embodiment of the invention, on departing the measuring chamber, the destination of the proportion of the fluid mixture (eg a discrete component) may be controlled so tat it is directed along a first path. Preferably, second and subsequent proportions of the fluid mixture (eg second and subsequent discrete components) are directed elsewhere (eg along second and subsequent paths). For example the two components of a binary system may be directed along discrete paths to two separate destinations.

In one embodiment of the method of the invention, the step of causing the proportion of the fluid mixture to flow to a unique destination remote from the remainder of the fluid mixture may be carried out by sending an appropriate signal to a separating means in or adjacent to the flow path when the predetermined target is attained. The separating means may be a deflecting means in the flow path. For example, the deflecting means may be one or more valves or a baffle system.

In an embodiment of the invention, the electrical signal is a time varying electrical signal. For example, the time varying electrical signal may be periodic. Preferably, the time varying electrical signal is an alternating current (AC) signal. Preferably the electrical signal is a sine wave varying in either voltage or current. A means for varying the resonant frequency of the applied electrical signal may be used. For example, at least one inductor or one or more quartz crystal resonators may be added in series or parallel. Conveniently, the means for varying the frequency of the applied electrical signal ensures that the resonant frequency is below about 1 MHz. At such a resonant frequency, problems associated with instrumentation and digitisation are generally reduced. Alternatively higher frequencies (eg 500 MHz-1 GHz) may be used. As such this allows the parasitic inductances and capacitances be used.

The measurement of the impedance quantity may comprise a time to frequency domain transformation of the time varying electrical signal. The steps involved in such a measurement will be generally familiar to those skilled in the art (see for example Perturbation Signals for System Identification, ed K Godfrey, Prentice Hill, 1993, UK). The time varying electrical signal may be periodic and may comprise may suitable function or code eg a pseudo random binary sequence (PRBS), a Golay code, a Walsh function, a Huffman sequence or any other suitable coded sequence. Other suitable signals, codes or methodologies such as white Gaussian noise or wavelet analysis, impulse response to step response may be employed and will be generally familiar to those skilled in the art (see for example Signal Processing Methods for Audio Images and Telecommunications, ed P M Clarkson and H Stork, Academic Press, London, 1995).

Viewed from a further aspect the present invention provides an apparatus for isolating a proportion of a fluid mixture (eg a discrete component such as cells or particles) from the fluid mixture as a whole, said apparatus comprising:

an electrical impedance measuring device adapted to permit the fluid mixture to flow through a measuring chamber, wherein said device is capable of measuring an impedance quantity characteristic of the proportion of the fluid mixture in the measuring chamber; separating means in or adjacent to the flow path of the fluid mixture at or near to the exit end of the measuring chamber; and means for sending a signal to the separating means when the impedance quantity attains a predetermined target whereby to cause the proportion of the fluid mixture to flow to a unique destination remote from the remainder of the fluid mixture.

The separating means may be a deflecting means in the flow path. For example, the deflecting means may be one or more valves or a baffle system.

In a preferred embodiment, the electrical impedance measuring device comprises an electrical signal applying means adapted to apply a time varying electrical signal to the measuring chamber at one or more frequencies in a frequency range (preferably including a resonant frequency) and measuring means for measuring an impedance quantity characteristic of the proportion of the fluid mixture in a measuring chamber at the one or more frequencies in the frequency range. In an embodiment of the apparatus of the invention, the electrical signal applying means is capable of applying an ac signal of variable frequency. In an embodiment of the apparatus of the invention, the electrical signal applying means is capable of applying a variable electrical signal sine wave varying in either voltage or current. In an embodiment of the apparatus of the invention, the electrical signal applying means is capable of applying a time varying electrical signal which is periodic. The electrical signal applying means may comprise a means for varying the frequency of the electrical signal to apply the electrical signal at a plurality of frequencies in a range including the resonant frequency. For example, the apparatus may further comprise at least one inductor or at least one quartz crystal resonator. Conveniently, the means for varying the frequency of the electrical signal is arranged so that the resonant frequency is below about 1 MHz. At such a resonant frequency, problems associated with instrumentation and digitisation are generally reduced.

The electrical signal applying means may comprise at least two electrodes (eg gold microelectrodes). Numerous electrode materials, sizes and configuration are suitable (as desired) for the preferred embodiment. In a preferred embodiment of the apparatus of the invention, the electrical signal applying means comprises one or more microelectrodes of the type generally or specifically disclosed in WO-A-99/60392 (Farfield Sensors Limited) or specifically claimed therein.

In one embodiment, the measuring chamber is configured so that measurement of impedance quantities may be conducted in an effective 1-dimensional electric field. For example, the measuring chamber may take the form of a microchamber or microchannel. For example, the measuring chamber may have the dimensions 5.times.3.times.2 microns. The microchamber or microchannel may be lined with one or more microelectrodes in the manner described by Ayliffe (supra).

In an embodiment of the apparatus of the invention, the measuring means may comprise an impedance analyser. In an embodiment of the apparatus of the invention, the measuring means may be capable of performing a time to frequency domain transformation of the time varying electrical signal.

Fluid transport methodologies for achieving flow of the fluid mixture through the measuring chamber are familiar to those skilled in the art. A suitable method involves capillary flow techniques.

The volume of the proportion of fluid mixture which may be subjected to the method of the invention will be generally determined by the amount of fluid mixture which can flow through the electrical impedance measuring device and is processed. Ayliffe et al (supra) have demonstrated that a measuring chamber with a volume approaching 120 fl may be used. The volume of the proportion of fluid mixture capable of being processed then depends upon the time taken to effect a measurement of the impedance quantity of the proportion of fluid mixture in the measuring chamber. This varies depending upon the instrument used for measuring the impedance quantity. For example, a Hewlett Packard 4192A impedance analyser is capable of conducting approximately 6 measurements per second at a single frequency. In practice, it is desirable to have a flow rate slower than the minimum time taken to conduct a measurement thereby to prevent proportions of the fluid mixture (eg discrete components) flowing through the measuring chamber and avoiding measurement cycles. An HP 4192A analyser has a measurement rate which permits a volume of approximately 500 fl per second to be processed (120 fl measuring cell volume times.4 measurements per second). Using a faster measurement regime allows greater volumes to be processed.

In an embodiment of the apparatus, a plurality of electrical impedance measuring devices and separating means acting in parallel may be fed from a single source of fluid mixture. This would enable the volume throughput to be advantageously increased.

In general, there will be a finite volume of fluid mixture between the measuring chamber and the separating means (eg switching valve) which directs the flow to the desired destination. In order to synchronise the detection mechanism and the valve opening, it may be assumed that at a constant flow rate it will take a time (t) for the proportion of the fluid mixture in the measuring chamber to be flushed out and flow to the valve. Once the impedance quantity (eg spectrum) of the proportion of fluid mixture is measured in the measuring chamber, the control signal may be delayed by time t. As such, the opening and closing of the valve will coincide with the arrival of the proportion of the fluid mixture which was in the measuring chamber t seconds ago. In practice, t may be reduced slightly to take into account the fact that the measurement may have been conducted on a part of the proportion of the fluid mixture (ie the proportion could already be leaving the measuring chamber once the impedance measurement was made). As such, it would be an advantage to open the valve slightly ahead of the proportion of fluid mixture to increase the effectiveness of isolation.

In a preferred embodiment of the method of the invention, the step of causing the proportion of fluid mixture to flow to a unique destination may be repeated through secondary measuring chambers and separating means to improve the effectiveness of isolation. Further measuring chambers and separating means may be used if desired. Alternatively the proportion of fluid mixture may be recycled through the same measuring chamber and separating means to optimise isolation.

In recognizing that the impedance characteristics of a fluid sample which has been made part of a resonant electrical circuit are a useful analytical tool, other patentably significant aspects of the invention have been envisaged.

Viewed from a further aspect the present invention provides a method for screening a fluid medium for the presence of an analyte, said method comprising:

allowing the fluid medium to flow through a measuring chamber;

applying an electrical signal at one or more frequencies to the proportion of the fluid mixture in the measuring chamber;

measuring an impedance quantity characteristic of the proportion of the fluid mixture in the measuring chamber at the one or more frequencies; and comparing the impedance quantity of the proportion of the fluid medium measured in the measuring chamber with a known impedance quantity of the analyte.

The method is particularly advantageous for screening a very small volume of a fluid sample in a microchamber where the measured impedance quantity (eg spectrum) of that volume of the sample is a fingerprint ie characteristic of the proportion of the fluid in the microchamber.

Viewed from a yet further aspect the present invention provides a method for quantifying the presence of an analyte in a fluid medium, said method comprising:

allowing the fluid medium to flow through a measuring chamber;

applying an electrical signal at one or more frequencies to the proportion of the fluid mixture in the measuring chamber;

measuring an impedance quantity characteristic of the proportion of the fluid mixture in the measuring chamber at the one or more frequencies, and activating an audible or visual response when the impedance quantity of the proportion of the fluid medium measured in the measuring chamber attains a predetermined target (eg is at or near to or exceeds a predetermined target level of the impedance quantity).

The method is particularly advantageous for "counting" an analyte in a very small volume of a fluid sample in a microchamber where the measured impedance quantity (eg spectrum) of the volume of the sample is a fingerprint ie characteristic of the proportion of the fluid in the microchamber.

Preferably the audible or visual response is activated when the measured impedance quantity exceeds the known impedance quantity of the component of the fluid in which the analyte is suspended.

DETAILED DESCRIPTION OF THE PREFERRED EMBODIMENTS

The present invention will now be described in a non-limitative sense with reference to the accompanying Figures in which:

FIG. 1 is a schematic representation of an embodiment of the method and apparatus of the invention for separating an analyte from a solution.

In FIG. 1, there is represented an apparatus according to the invention designated generally by reference numeral 1. A single source of a weak analyte (A) in solution 2 was fed by means of a pump 3 to an electrical impedance measuring device 4. The electrical impedance measuring device 4 comprises a measuring chamber 5 together with a measurement and control system 6. The measurement system may take the form of an HP4192A analyser. At the exit end of the measuring chamber, there is located a twin valve mechanism 7 which is responsive to signals from the control system 6.

As the solution of analyte 2 is pumped through the measuring chamber 5, an impedance quantity is measured at one or more frequencies of the electrical signal which is applied. The measured impedance quantity is then compared to a database containing the known impedance quantity of A by control system 6. When a match occurs, valve 7a is closed and valve 7b is opened so that the component A alone passes from the measuring chamber to the beaker 8. When no match occurs, valve 7a is opened is valve 7b is closed so that components in the solution 2 other than analyte A pass to the waste beaker 9.

What is claimed is:

1. A method for isolating a proportion of a fluid mixture from the fluid mixture as a whole, said method comprising:
    allowing the fluid mixture to flow through a measuring chamber;
    applying an electrical signal at one or more frequencies to the proportion of the fluid mixture in the measuring chamber;
    measuring an impedance quantity characteristics of the proportion of the fluid mixture in the measuring chamber at the one or more frequencies; and
    causing the proportion of the fluid mixture to flow to a unique destination remote from the remainder of the fluid mixture when the impedance quantity measured at the one or more frequencies attains a target impedance quantity.

2. A method as claimed in claim 1 wherein the target impedance quantity is a calibrated impedance quantity.

3. A method as claimed in claim 1 wherein the measuring chamber is a microchamber.

4. A method as claimed in claim 1 wherein the proportion of the fluid mixture is a discrete component selected from the group consisting of cells and particles.

5. A method as claimed in claim 1 wherein the one or more frequencies at which the impedance quantity is measured includes a resonant frequency.

6. A method as claimed in claim 1 wherein the impedance quantity is the dissipation factor.

7. A method as claimed in claim 1 wherein the electrical signal is applied at each of a plurality of frequencies in a frequency range and the impedance quantity is measured at each of the plurality of frequencies in the frequency range.

8. A method as claimed in claim 7 wherein the plurality of frequencies includes a resonant frequency.

9. A method as claimed in claim 8 wherein the plurality of frequencies in the range are sufficient in number to generate an impedance spectrum characteristic of the proportion of the fluid mixture in the measuring chamber.

10. A method as claimed in claim 1 wherein the electrical signal is applied at a single frequency and the impedance quantity is measured at that frequency.

11. A method as claimed in claim 10 wherein the single frequency is at or near to the resonant frequency of the measuring chamber containing the proportion of the fluid mixture.

12. A method as claimed in claim 4 wherein the volume of the proportion of fluid mixture in the measuring chamber is less than $10^{-6}$ liters.

13. A method as claimed in claim 12 wherein the fluid mixture is a binary system.

14. A method as claimed in claim 12 wherein the fluid mixture comprises two or more liquids.

15. A method as claimed in claim 13 wherein the fluid mixture comprises a liquid (or mixture of liquids) with one or more dissolved or suspended components.

16. A method as claimed in claim 15 wherein the fluid mixture comprises particles or cells suspended in a liquid medium.

17. A method as claimed in claim 16 wherein the fluid mixture is a blood extract consisting essentially of blood cells and liquid medium.

18. A method as claimed in claim 12 wherein the fluid mixture is a solution.

19. A method as claimed in claim 18 wherein the solution is a polymer containing solution.

20. A method as claimed in claim 2 further comprising the initial steps of:
    allowing a calibrant fluid mixture to flow through a measuring chamber,
    applying an electrical signal at one or more frequencies to the proportion of the calibrant fluid mixture in the measuring chamber;
    measuring the calibrated impedance quantity of the proportion of the calibrant fluid mixture in the measuring chamber at the one or more frequencies; and
    correlating the calibrated impedance quantity of the proportion of the calibrant fluid mixture in the measuring chamber with a characteristic of the proportion of the calibrant fluid mixture in the measuring chamber, wherein the characteristic of the proportion of the calibrant fluid mixture in the measuring chamber is known.

21. A method as claimed in claim 20 further comprising:
    comparing the impedance quantity of the proportion of the fluid mixture measured in the measuring chamber with the calibrated impedance quantity.

22. A method as claimed in claim 21 comprising:
causing the proportion of the fluid mixture to flow to a unique destination when the impedance quantity measured at the one or more frequencies is substantially the same as the target impedance quantity at the one or more frequencies.

23. A method as claimed in claim 21 comprising:
causing the proportion of the fluid mixture to flow to a unique destination when the impedance quantity measured at the one or more frequencies is above the target impedance quantity.

24. A method as claimed in claim 21 further comprising:
sending an appropriate signal to a separating means in or adjacent to the flow path when the target impedance quantity is attained.

25. A method as claimed in claim 20 wherein the electrical signal is a time varying electrical signal.

26. An apparatus for isolating a proportion of a fluid mixture from the fluid mixture as a whole, said apparatus comprising:
an electrical impedance measuring device adapted to permit the fluid mixture to flow through a measuring chamber, wherein said device is capable of measuring an impedance quantity characteristic of the proportion of the fluid mixture in the measuring chamber;
separating means in or adjacent to the flow path of the fluid mixture at or near to the exit end of the measuring chamber; and
means for sending a signal to the separating means when the impedance quantity attains a target impedance quantity whereby to cause the proportion of the fluid mixture to flow to a unique destination remote from the remainder of the fluid mixture.

27. An apparatus as claimed in claim 26 wherein the separating means is a deflecting means in the flow path.

28. An apparatus as claimed in claim 26 wherein the electrical impedance measuring device comprises:
an electrical signal applying means adapted to apply a time varying electrical signal to the measuring chamber at one or more frequencies in a frequency range; and
measuring means for measuring an impedance quantity characteristic of the proportion of the fluid mixture in a measuring chamber at the one or more frequencies in the frequency range.

29. An apparatus as claimed in claim 28 wherein the electrical signal applying means comprises at least two microelectrodes.

30. An apparatus as claimed in claim 26 wherein the measuring chamber is configured so that measurement of an impedance quantity is conducted in an effective 1-dimensional electric field.

31. An apparatus as claimed in claim 30 wherein the measuring chamber is a microchamber or microchannel.

* * * * *